United States Patent
Kleiner et al.

(10) Patent No.: US 9,205,575 B2
(45) Date of Patent: *Dec. 8, 2015

(54) MEDICAL DEVICE FABRICATION PROCESS INCLUDING STRAIN INDUCED CRYSTALLIZATION WITH ENHANCED CRYSTALLIZATION

(71) Applicant: Abbott Cardiovascular Systems Inc., Santa Clara, CA (US)

(72) Inventors: Lothar W. Kleiner, Los Altos, CA (US); Fuh-Wei Tang, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,215

(22) Filed: May 15, 2014

(65) Prior Publication Data

US 2014/0252675 A1    Sep. 11, 2014

Related U.S. Application Data

(63) Continuation of application No. 13/077,635, filed on Mar. 31, 2011, now Pat. No. 8,765,040, which is a continuation-in-part of application No. 12/465,570, filed on May 13, 2009, now Pat. No. 8,372,332, which (Continued)

(51) Int. Cl.
*B29C 49/00* (2006.01)
*B29C 35/02* (2006.01)

(Continued)

(52) U.S. Cl.
CPC .............. *B29C 35/16* (2013.01); *B29C 45/0055* (2013.01); *B29C 47/0038* (2013.01); *B29C 71/02* (2013.01); *B29L 2031/7534* (2013.01)

(58) Field of Classification Search
USPC ......... 264/514, 515, 519–521, 523, 534, 540, 264/563, 564, 567, 573, 171.26, 178 R, 264/209.1, 209.4, 209.5, 211, 211.13, 235, 264/237, 346, 348
See application file for complete search history.

(56) References Cited

U.S. PATENT DOCUMENTS 6,388,043 B1   5/2002  Langer et al.
6,719,935 B2   4/2004  Tunc
(Continued)

FOREIGN PATENT DOCUMENTS

JP   2006-519672    8/2006
WO   WO 2004/080332   9/2004

OTHER PUBLICATIONS

A Notice of Reason for Rejection from JPO, dated May 27, 2014, for Appl. No. JP2012-510882, 2 pgs.

(Continued)

*Primary Examiner* — Ryan Ochylski
(74) *Attorney, Agent, or Firm* — Squire Patton Boggs (US) LLP

(57) ABSTRACT

Methods of fabricating a polymeric implantable device, such as a stent, with improved fracture toughness through annealing a polymer construct below the glass transition temperature of the polymer of the construct prior to a deformation step are disclosed herein. The deformation of the construct induces crystallization in the polymer construct through strain-induced crystallization. The annealing of the polymer construct accelerates the crystallization induced during the deformation and results in an increase in crystallite density with smaller crystallites as compared to deformation of a tube that has not been annealed. A stent scaffolding is then made from the deformed tube.

13 Claims, 7 Drawing Sheets

Related U.S. Application Data is a continuation-in-part of application No. 12/189,620, filed on Aug. 11, 2008, now Pat. No. 8,394,317, said application No. 13/077,635 is a continuation-in-part of application No. 12/764,803, filed on Apr. 21, 2010, now abandoned.

(51) Int. Cl.
  *B29C 35/16* (2006.01)
  *B29C 71/02* (2006.01)
  *B29C 45/00* (2006.01)
  *B29C 47/00* (2006.01)
  *B29L 31/00* (2006.01)

(56) References Cited

U.S. PATENT DOCUMENTS

| | | | |
|---|---|---|---|
| 7,329,366 | B1 | 2/2008 | Gale et al. |
| 7,740,791 | B2 | 6/2010 | Kleine et al. |
| 8,501,290 | B2 | 8/2013 | Wang |
| 8,545,546 | B2 | 10/2013 | Wang |
| 8,613,880 | B2 | 12/2013 | Wang et al. |
| 8,703,038 | B2 | 4/2014 | Wang et al. |
| 8,765,040 | B2 * | 7/2014 | Kleiner et al. ............. 264/235 |
| 8,852,263 | B2 | 10/2014 | Wang |
| 2007/0283552 | A1 | 12/2007 | Gale et al. |
| 2008/0147165 | A1 | 6/2008 | Hossainy et al. |
| 2008/0177374 | A1 | 7/2008 | Zheng et al. |
| 2009/0036972 | A1 | 2/2009 | Gale et al. |
| 2009/0111787 | A1 | 4/2009 | Lim et al. |
| 2014/0225311 | A1 | 8/2014 | Kleine et al. |
| 2014/0374963 | A1 | 12/2014 | Kleiner et al. |

OTHER PUBLICATIONS

The translation of the Notice of Reason for Rejection from JPO, dated May 27, 2014, for Appl. No. JP2012-510882, 2 pgs.
Goto et al., "Effect of annealing on deformation and fracture behavior of injection molded PLA", J. of the Japanese Soc. For Strength and Fracture of Materials, vol. 42, No. 1, pp. 7-10 (2008).

* cited by examiner

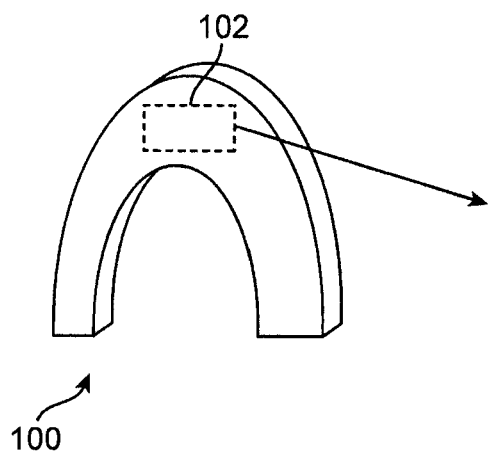 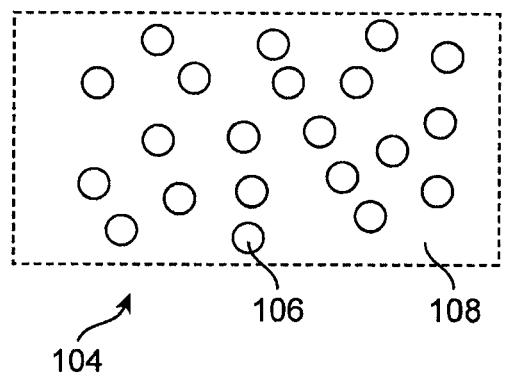
FIG. 4A　　　　　　　FIG. 4B
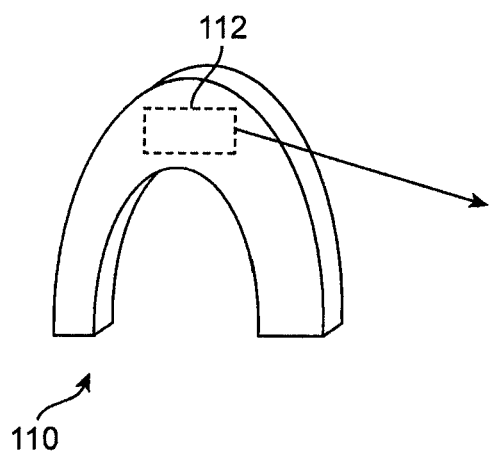 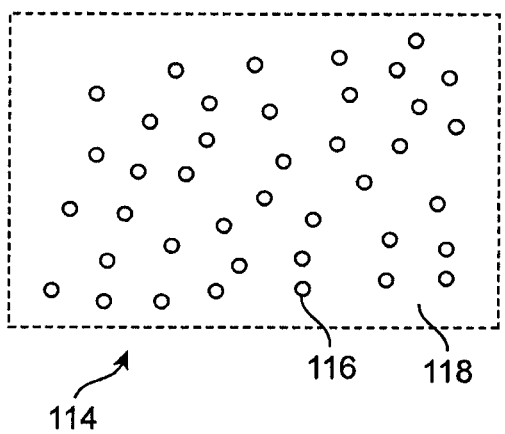
FIG. 5A　　　　　　　FIG. 5B

MEDICAL DEVICE FABRICATION PROCESS INCLUDING STRAIN INDUCED CRYSTALLIZATION WITH ENHANCED CRYSTALLIZATION

This application is a continuation of application Ser. No. 13/077,635 filed Mar. 31, 2011, which is a continuation-in-part of application Ser. No. 12/465,570 filed on May 13, 2009, which is a continuation-in-part of application Ser. No. 12/189,620 filed on Aug. 11, 2008. Application Ser. No. 13/077,635 is also a continuation-in-part of application Ser. No. 12/764,803 filed on Apr. 21, 2010. All of these applications are incorporated by reference herein.

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating a stent in whole or in part from materials that erode or disintegrate through exposure to conditions within the body. Stents fabricated from biodegradable, bioabsorbable, and/or bio-erodable materials such as bioabsorbable polymers can be designed to completely erode only after the clinical need for them has ended.

However, there are several challenges is making a bioabsorbable polymeric stent. These include making a stent with sufficient radial strength, stiffness, and toughness or resistance to fracture. Another challenge is addressing physical aging. Medical devices are typically storage for an indefinite period of time after fabrication. During storage physical aging causes the physical properties of the polymer to change as a function of time. Since storage time will vary for each device that is made, the problem of product consistency arises.

SUMMARY OF THE INVENTION

Various embodiments of the present invention include a method of making a stent comprising: annealing an extruded PLLA tube at a temperature greater than 37° C. and less than or equal to Tg,midpoint or Tg,midpoint temperature range of the PLLA extruded tube; wherein the PLLA tube is annealed for a selected annealing time greater than 1 min; wherein the annealing increases the nucleation density of the PLLA tube; followed by radially expanding the PLLA tube, wherein the radial expansion induces crystallization in the PLLA tube, wherein the increase in nucleation density due to the annealing results in the formation of a higher crystallite density and a decrease in the size of the crystallites as compared to tube that has not been annealed; and fabricating a stent scaffolding from the expanded PLLA tube.

BRIEF DESCRIPTION OF THE DRAWINGS

FIG. 4A depicts a strut of a polymeric stent fabricated without annealing.

FIG. 4B is a schematic microstructure of a section of the strut of FIG. 4A.

FIG. 5A depicts a strut of a polymeric stent fabricated with annealing.

FIG. 5B is a schematic microstructure of a section of the strut of FIG. 5A.

DETAILED DESCRIPTION OF THE INVENTION

Various embodiments of the present invention relate to manufacture of polymeric implantable medical devices. In particular, the embodiments include methods of making an implantable medical device from a polymer construct that includes subjecting the construct to an annealing step which include annealing or aging the construct at an elevated temperature below the glass transition temperature (Tg) of a polymer of the construct followed by a deformation step in which the annealed polymer construct is deformed. The Tg refers to the glass transition temperature of the semi-crystalline polymer prior to the annealing step. The deformation step results in strain-induced crystallization in the construct. The annealing step provides several advantages including one or more of the following: higher crystallinity, higher density of smaller crystallites, faster crystallization kinetics, reduced physical aging, and improved mechanical properties, for example, higher modulus, and higher toughness. The higher density, smaller crystallites provide increased toughness in the polymer construct and a device fabricated from the annealed and deformed polymer constructed.

The methods described herein are generally applicable to any semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
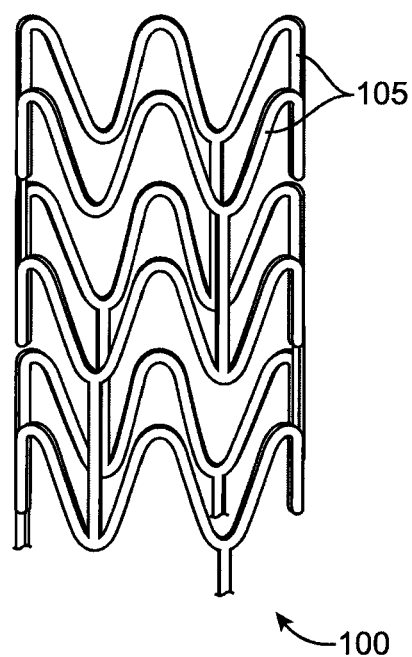
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device of the present invention can be made partially or completely from a biodegradable, bioresorbable, bioabsorbable, or biostable polymer. A polymer for use in fabricating an implantable medical device can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from several months to a few years. The duration is typically up to about six months, twelve months, eighteen months, or two years. In some situations, the treatment period can extend beyond two years.

As indicated above, a stent has certain mechanical requirements such as high radial strength, high stiffness or high modulus, and high fracture toughness. A stent that meets such requirements greatly facilitates the delivery, deployment, and treatment of a diseased vessel. With respect to radial strength and stiffness, a stent must have sufficient radial strength to withstand structural loads, namely radial compressive forces, imposed on the stent so that the stent can supports the walls of a vessel at a selected diameter for a desired time period. A polymeric stent with inadequate radial strength and/or stiffness can result in an inability to maintain a lumen at a desired diameter for a sufficient period of time after implantation into a vessel.

In addition, the stent must possess sufficient toughness or resistance to fracture to allow for crimping, expansion, and cyclic loading. These aspects of the use of the stent involve deformation of various portions of the stent. Sufficient toughness is important to prevent cracking or fracture during use which could lead to premature mechanical failure of the stent.

The strength to weight ratio of polymers is usually smaller than that of metals. To compensate for this, a polymeric stent can require significantly thicker struts than a metallic stent, which results in an undesirably large profile. The strength deficiency of polymers is addressed in the present invention by incorporating a deformation step in the stent fabrication process by subjecting the polymer construct to deformation. Deforming polymers tends to increase the strength along the direction of deformation, which is believed to be due to the induced polymer chain orientation along the direction of deformation. For example, radial expansion of a polymeric tube construct provides preferred circumferential polymer chain orientation in the tube. Additionally, stretching a tube provides preferred axial orientation of polymer chains in the tube. Thus, a stent fabrication process can include radially deforming a polymer tube and cutting a stent from the deformed tube. The deformation process also results in strain induced crystallization, increasing the crystallinity of the construct which increases the strength of the polymer.

Semi-crystalline polymers that are that are stiff or rigid under biological conditions or conditions within a human body are particularly suitable as stent materials. Specifically, polymers that have a glass transition temperature (Tg) sufficiently above human body temperature which is approximately 37° C., should be rigid upon implantation. Poly(L-lactide) (PLLA) is an example of such a polymer. These polymers, however, may exhibit a brittle fracture mechanism in which there is little or no plastic deformation prior to failure. As a result, it is important not only to improve the strength of such polymers when making a device, but also to improve the fracture toughness for the range of use of a stent, specifically for the range deformation during use of the stent. In particular, it is important for a stent have high resistance to fracture throughout the range of use of a stent, i.e., crimping, delivery, deployment, and during a desired treatment period after deployment.

The morphology of semi-crystalline polymer can include crystalline regions (crystallites or spherulites) embedded or dispersed in amorphous regions. Fracture toughness of semi-crystalline polymers is positively correlated with a high density of small crystallites. Thus, fracture toughness is improved by processing which results in smaller crystallites and increasing the their density.

Generally, in the crystallization of polymers, there are two separate events that occur. The first event is the formation of nuclei in the amorphous polymer matrix. The second event is growth of the crystallite around these nuclei. The overall rate of crystallization of the polymer is dependent, therefore, on the equilibrium concentration of nuclei in the polymer matrix, and on the rate of growth of crystallites around these nuclei.

Semi-crystalline polymers can contain both amorphous and crystalline domains at temperatures below the melting point of the polymer. Amorphous regions are those in which polymer chains are in relatively disordered configurations. Crystalline domains or crystallites are those in which polymer chains are in ordered configurations with segments of polymer chains essentially parallel to one another.

With respect to physical aging, a medical device typically is stored for an indefinite period of time prior to use in a patient which can be days, weeks, or months and is typically not the same for every individual device. Polymers, particularly polymers that are at least partially amorphous such as semi-crystalline polymers, generally undergo physical aging during storage when the glass transition, Tg, of the amorphous region is greater than the storage temperature. Physical aging corresponds to densification or a volumetric shrinkage of the amorphous regions of a polymer. Physical aging occurs when an amorphous material is cooled rapidly below its Tg, it typically leads to non-equilibrium condition due to the presence of excess free volume. The mobility of the molecules with excess free volume within the glassy state will cause the system to relax and increase in density over time. The densification causes a change in material properties of the polymer with time. For semi-crystalline polymers, the densification occurs in the amorphous regions of the polymer.

The processing history of a polymer stent can result in physical aging during storage. A manufacturing process of a polymeric stent can include, but is not limited to, obtaining a polymeric tube formed by a melt processing method, such as extrusion or injection molding. The melt processing methods involve cooling at a non-equilibrium rate that results in excess free volume which leads to densification during storage. Therefore, devices with different temperature histories, storage times, or both can have inconsistent properties.

Figure 2:
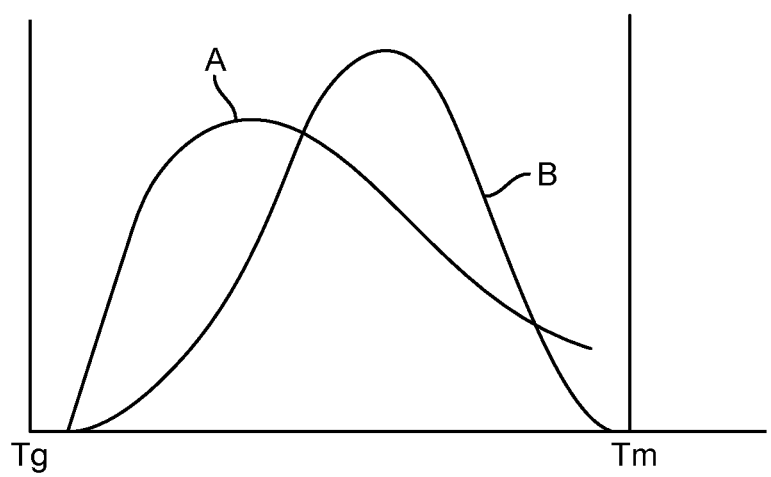
FIG. 2 depicts a schematic plot of the crystal nucleation rate and the crystal growth rate for a polymer.

In general, crystallization tends to occur in a polymer at temperatures between the Tg and the melting point (Tm) of the polymer. FIG. 2 shows a schematic of the dependence of nucleation rate (A) and crystal growth rate (B) on temperature between the Tg and the Tm under quiescent conditions. Crystallization under quiescent conditions refers to crystallization in the absence of applied stress or deformation. At temperatures above Tg but far below Tm where polymer chain mobility is limited, nucleation is highly favored over crystal growth, since the latter process requires much more extensive chain mobility. These nuclei remain present in the polymer until its temperature is elevated above Tm for a period of time. A consequence of the behavior illustrated in FIG. 2 is that at high temperatures between Tg and Tm there are relatively few, large crystallites formed, while at low temperatures between Tg and Tm, there are relatively more numerous, smaller crystallites formed.

Figures 3A, 3B, 3C:
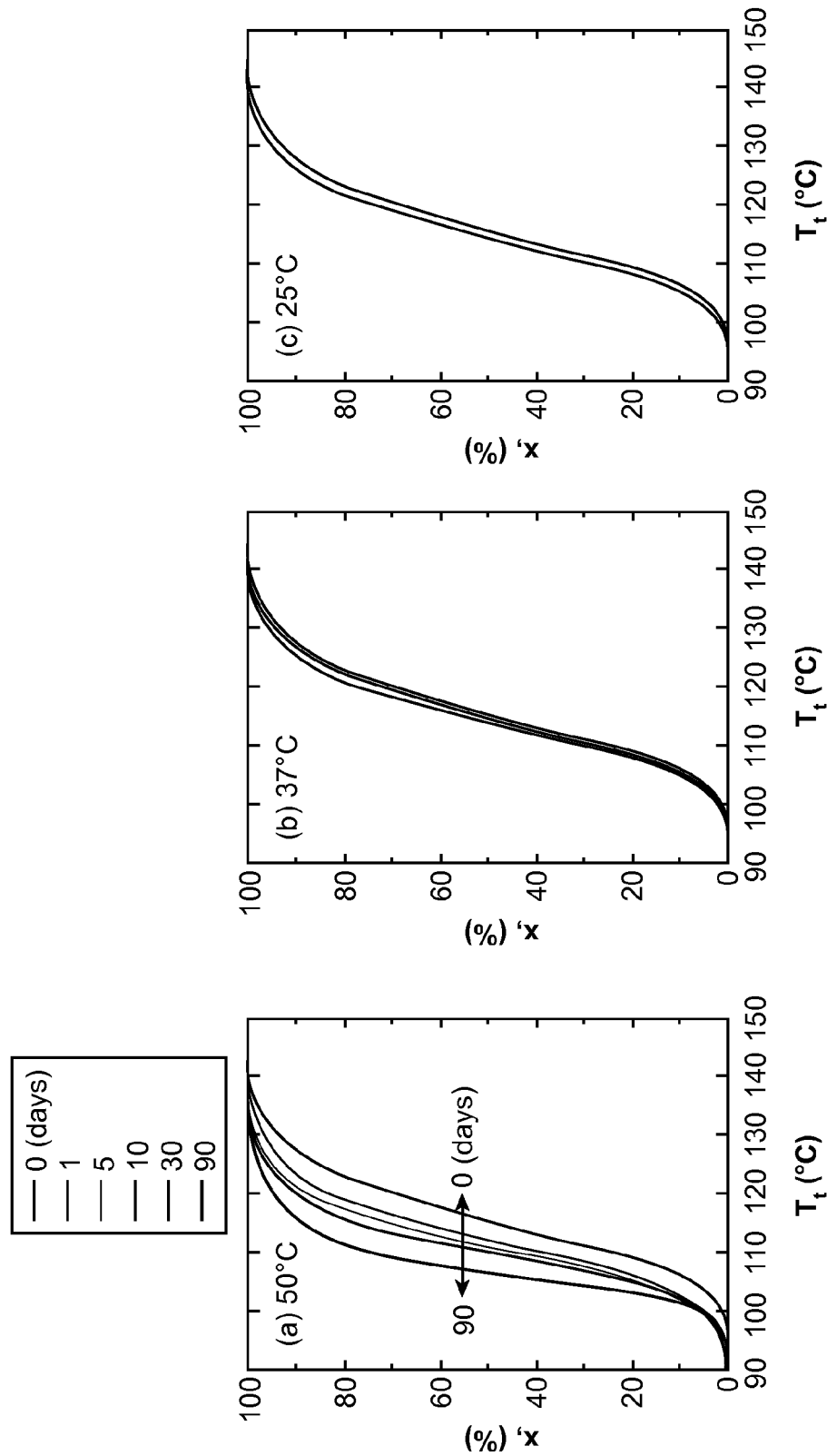
FIGS. 3A-C shows the relative crystallinity (Xr) of melt-quenched PLLA physically aged at 25° C. (a), 37° C. (b), and 50° C. (c) as a function of crystallization temperature (Tc) during DSC heating.

Tsuji et al. investigated the effect of physical aging or annealing on the nonisothermal crystallization of PLLA for a wide temperature range below Tg for 90 days. J. of Applied Polymer Science Vol. 116, Issue 2, pages 1190-1196, 15 Apr. 2010 (incorporated by reference herein). In this investigation, low-temperature physical aging of amorphous PLLA was carried out at temperatures between 25-50° C. for 90 days. The aged samples were then heated above the glass transition temperature to above the melting point. It was found that the physical aging significantly increased the Tg and glass transition enthalpy, but did not cause crystallization, regardless of aging temperature. However, it was shown that the nonisothermal crystallization of PLLA during heating was accelerated only by physical aging at 50° C. FIG. 3A-C (FIG. 5 from Tsuji et al.) shows the relative crystallinity (Xr) of melt-quenched PLLA physically aged at 25° C. (3A), 37° C. (3B), and 50° C. (3C) as a function of crystallization temperature (Tc) during DSC heating.

It is believed by the inventors that the aging at 50° C. increased the nucleation density of the PLLA without any crystal growth. The increased nucleation density accelerated crystallization kinetics or rate when the sample was heated above Tg. The increased nucleation which caused a higher crystallization rate resulted in a higher relative degree of crystallization for the samples aged at 50° C. than the samples that either were not aged or that were aged at the lower temperatures. The data in Tsuji et al., however, applies to crystallization under quiescent conditions and no data on the effect of aging on strain-induced crystallization is provided in Tsuji.

Various embodiments of the present invention include a method of making an implantable medical device from a polymer construct made partially or completely of a semi-crystalline polymer. In some embodiments, the polymer construct is a tube, from which a stent is made. The method further includes aging or annealing the polymer construct at a temperature below the Tg of the semi-crystalline polymer.

The temperature is selected to obtain accelerated crystallization when the aged or annealed construct is subjected to a deformation step or a strain-induced crystallization step. The annealing does not increase the crystallinity of the polymer construct. It is believed that the annealing increases the nucleation density. After the aging or annealing step, the polymer construct is deformed resulting in strain-induced crystallization. In the case of an extruded polymeric tube, the deformation step includes radially expanding and axially elongating the tube. The method further includes additional processing steps for making a device, which for stent includes forming a scaffold from the tube, optionally coating the scaffold, and crimping the scaffold over a support.

In the above embodiments, aging or annealing a construct may refer to or include heating the construct to a temperature in a selected temperature range. Aging or annealing may refer to or include maintaining the temperature of the construct in a selected temperature range for selected period of time. Aging or annealing a construct may refer to or include subjecting or exposing a construct to a temperature in a selected temperature range for a selected period of time. In some embodiments, the annealing or aging can also include cooling or allowing the annealed construct to below the annealing temperature. The construct may be cooled or be allowed to cool to ambient or room temperature, which may be any temperature between and including 20 to 30° C. The annealed construct may cooled by exposing it to a selected cooling temperature, such as room temperature, which can be any temperature between 20 and 30° C., or a temperature below room temperature, such as below 30° C. The annealed construct can be cooled by blowing cooled gas on the construct, disposing the construct in a refrigerator or freezer, or immersing the construct in a liquid, such as water. The annealed construct may also be quenched from the annealing temperature to a lower temperature. Quenching the construct refers to an extremely rapid cooling or extremely rapid reduction of the temperature of the polymer construct from the annealing temperature to a lower temperature such as room temperature or below room temperature, for example, 10-30° C. below room temperature. The quenching can be achieved by contacting the construct with a chilled quenching medium such as chilled water or circulation or chilled gases that are 10-30° C. below room temperature or lower than 30° C.

In the various embodiments of the invention, the polymer construct can be made by a melt processing method such as extrusion or injection molding. Unless otherwise specified, when referring to the present invention, the Tg referred to herein is the Tg of a melt processed construct, such as an extruded tube. Prior to the annealing step, the polymer construct may be completely amorphous (100% amorphous, 0% crystallinity) or have a crystallinity of 0 to 5%, 5-15%, less than 15%, or greater than 15%. The semi-crystalline polymer of the polymer construct may have a number average molecular weight Mn of at least 80 kD, at least 150 kD, or at least 200 kD. The semi-crystalline polymer of the polymer construct may have a number average molecular weight of less than 80 kD, 80-150 kD, 150-200 kD, 200-250 kD, or greater than 250 kD.

A polymer construct can be a polymer or polymer material formed into a geometrical shape, such as a tube or a sheet. The shape is chosen so that further processing can be applied to form selected implantable medical device. For example, the polymer construct can be a tube and a stent pattern can be cut into the tube to form a stent. A polymer tube has an inner diameter and an outer diameter and a thickness which is the outer diameter minus the inner diameter. The polymeric tube may be made completely out of the semi-crystalline polymer.

The polymer construct can be formed using a melt processing technique, such as extrusion or injection molding. Alternatively, a polymer tube may be formed from a sheet that is rolled and bonded into a tube. The deformation step in the case of tube can include radial expansion of the tube, axial elongation of the tube, or both.

In some embodiments, the polymer construct may be free of nucleating agents such as particulate nucleating agents or contain less than 0.01 wt % of such agents. In other embodiments, the polymer construct may be free of a particular drug or therapeutic agents or any drug or therapeutic agent, such as anti-proliferative agents or anti-inflammatory agents. The polymer construct may be porous (such as a network of pores having a dimension in the range of 100 nm to 10 microns, or more than 10 microns) or be nonporous.

In all embodiments of the present invention, the annealing temperature or range is below the Tg of the semi-crystalline polymer of the construct. If the construct includes more than one type of semi-crystalline polymer that are combined, then the annealing temperature is less than the Tg of at least one, some of the Tg's, or all of the Tg's of the types of semi-crystalline polymers. A type of polymer refers to the chemical identity of a monomer unit such as "L-lactide" or "glycolide." Polymers may be combined as random or alternating copolymers, block-copolymers, or blending types of polymers Annealing or aging at a temperature above the Tg of the semi-crystalline polymer of the tube when the tube is made of a single semi-crystalline polymer or above the Tg's of all the semi-crystalline polymers of the tube is not part of the present invention.

In some embodiments, the annealing temperature includes any temperature below Tg that results in accelerated crystallization that occurs when the construct is subjected to a deformation step or a strain-induced crystallization step. The accelerated crystallization corresponds to a higher crystallite density obtained from a deformation step of an annealed polymer construct compared to the crystallite density obtained in the deformation step of a polymer construct that has not been annealed.

The annealing temperature may be any temperature below Tg that results in an increase in nucleation density in a construct or a temperature that results in an increase in crystallite density upon deformation of the construct. A preferred range may be from 50° C. to Tg,onset or slightly below Tg,onset (e.g., up to 1% below Tg,onset) to Tg,midpoint, not including Tg,midpoint. For a PLLA extruded tube, Tg,onset is about 55° C. It is believed that in this range the increased mobility of the lower molecular weight components of the polymer is sufficient to create nuclei without crystal growth. At lower temperatures, such as 37, there is still insufficient mobility in the amorphous fraction to create nuclei; while at higher temperatures, the mobility of part of the amorphous fraction will be high enough to initiate nucleation as a result of annealing.

In some embodiments, the annealing temperature range may be 37° C. to Tg. In some embodiments the annealing temperature range may be Tg−20 to Tg, Tg−20 to Tg−5, Tg−20 to Tg−10, Tg−15 to Tg, Tg−15 to Tg−5, Tg−15 to Tg−10, Tg−10 to Tg, Tg−10 to Tg−5. For a PLLA extruded tube, the annealing temperature range may be 37-60° C., 40-60° C., 40-55° C., 40-50° C., 45-60° C., 45-55° C., 45-50° C., 50-60° C., 50-55° C., 50-58° C., 55- 60° C., 55-58° C., 52-57° C., or 53-55° C. The degree of increase of nucleation density from annealing and the degree of accelerated crystallization upon deformation depend on both the annealing temperature and the time or duration of annealing. The annealing time for any annealing temperature can be at least 1 hr, 1-12 hr, 12-24 hr, 1-3 days, 1-10 days, 1-30 days, 3-10 days, 10-30 days, 30-90 days, or greater than 90 days. The annealing time for any annealing temperature can be at least 1 hr, at least 12 hr, at least 24 hr, at least 1 day, at least 3 days, at least 10 days, or at least 30 days.

The annealing or aging of the construct can be performed by various methods. For example, the construct can be annealed or aged at the selected temperature in a vacuum oven. Alternatively, a warm gas which is the temperature of annealing such as nitrogen, oxygen, air, argon, or other gas can be blown on the construct. The temperature of the construct can be maintained by known control methods.

In certain embodiments, the deformation step can include radially expanding the polymeric tube (which induces preferred uniaxial circumferential orientation of polymer chains in the tube) or both radially expanding and axial elongating (inducing biaxial orientation of chains). The polymer tube is expanded from its initial diameter to a second diameter larger than the initial diameter, where the diameter can refer to the inner or outer diameter. The uniaxial/biaxial orientation increases the strength of the polymer of the tube in the circumferential direction due to the induced orientation. The increased strength of the polymer increases the radial strength of the tube and a stent made from the tube. The deformation induces crystallization which also increases the strength of the material and the radial strength of the tube and a stent made from the tube.

The temperature of the polymer construct is desirably above Tg during deformation since as stated in the definition of Tg below, Tg represents a transition from a vitreous state to a solid deformable or ductile state. Therefore, a temperature above Tg facilitates deformation of the polymer. Therefore, in certain embodiments, the polymer construct may be heated to a temperature above the Tg of the semi-crystalline polymer of the construct prior to or during the deformation. In certain embodiments, the deformation temperature is selected to favor a high crystallite density and smaller crystallites since such a morphology provides a high fracture toughness.

In certain embodiments, the polymer construct is heated from the annealing temperature to a deformation temperature above Tg and the construct is deformed. In embodiments, the polymer construct is not cooled below the annealing temperature between the end of then annealing time and the heating to the deformation temperature. In other embodiments, the construct is cooled or allowed to cool to a lower temperature at end of the annealing time prior to heating to the deformation temperature and deformation.

The deformed annealed construct has a higher density of crystallites that are smaller than for a construct that has not been annealed as described. It is believed that the annealing step increases the nucleation density of the construct which results in a higher density of and smaller crystallites upon deformation. Additionally, the increased nucleation density further provides higher fracture toughness since the nuclei generated during annealing grow into crystallites during deformation.

As indicated by the above discussion, deformation (expansion) increases both crystallinity and induces orientation. Both of these result in increasing the strength of the polymer. The induced orientation increases strength preferentially in the direction of orientation. The embodiments of the present invention provide a method of imparting the desired or a significant portion of the desired crystallinity and uniaxial/biaxial orientation in a single process step or at the same time, which is a significant advantage. Since inducing orientation increases crystallinity, the two features are much more readily controlled when performed in the same process step. In addition, the deformation is employed not only to increase crystallinity, but to impart a controllable uniaxial or biaxial orientation to polymer chains in the construct. The orientation improves both radial strength and fracture toughness that can be essential for the proper functioning of a device such as a stent.

FIG. 4A depicts a strut 100 of a polymeric stent after deformation fabricated without the annealing or aging step of the present invention and FIG. 4B is a schematic microstructure 104 of a section 102 of strut 100 showing a small amount of large crystals 106 dispersed within an amorphous region 108. FIG. 5A depicts strut 110 of a polymeric stent fabricated with the annealing or aging of the present invention. FIG. 5B depicts the schematic microstructure 114 of a section 112 of strut 110 showing a large amount of smaller crystals 116 dispersed within an amorphous region 118.

Exemplary semi-crystalline polymers that may be used in embodiments of the present invention include PLLA, poly(D-lactide) (PDLA), polyglycolide (PGA), (poly(L-lactide-co-glycolide) (PLGA), (poly(L-lactide-co-caprolactone) (PLCL), and PLLA-b-poly(ethylene oxide) (PLLA-b-PEO). Literature values of ranges of Tg and Tm of PLLA and PGA are given in Table 1.

TABLE 1

Tg and Tm for PLLA and PGA.

| Polymer | Melting Point (° C.)[1] | Glass Transition Temp (° C.)[1] |
|---|---|---|
| PGA | 225-230 | 35-40 |
| PLLA | 173-178 | 60-65 |

[1]Medical Plastics and Biomaterials Magazine, March 1998.

A desired final crystallinity after the deformation step of the construct may be at least 10%, 10-20%, 20-30%, 30-40%, 40-50%, or greater than 50%. However, a crystallinity above 50% may result in fracture toughness that is too low, i.e., brittle behavior that could result in fracture during crimping, deployment, and after deployment of a stent. A crystallinity of 15 to 50% is expected to provide adequate to superior strength and fracture toughness for a PLLA stent scaffolding.

After the deformation step, the construct can then be subjected to further processing steps in the device fabrication process, as described above.

In certain embodiments, the temperature of the polymer construct during deformation can be between Tg and Tm. For PLLA, the temperature range can be, for example, 10-90° C. above Tg. Lower temperatures, (e.g., 10-30° C. above Tg), are preferred since at such temperatures smaller crystallites resulting in a high density of smaller crystallites, as compared to higher deformation temperatures. As illustrated by FIG. 2, at lower temperatures the crystallization kinetics favor formation of nuclei over growth of existing crystallites. For a PLLA tube, the deformation temperature may be 70 to 105° C., or more narrowly, 70 to 90° C.

Crystallization during deformation can occur even at temperatures at which there is little or no crystallite growth at quiescent conditions. As stated above, the schematic curve (B) for the crystal growth rate in FIG. 2 corresponds to quiescent conditions, and, thus, does not necessarily apply to the crystallite growth during deformation. Specifically, the temperature dependence of nucleation growth vs. crystallite growth is not necessarily the same as under quiescent conditions.

In some embodiments, the polymer construct can be cooled or is allowed to cool to below the Tg of the semi-crystalline polymer of the construct. In other embodiments, the deformation step can be performed, followed by equilibrating the deformed construct at an increased temperature that allows further increase in crystallization in a temperature range of any of the disclosed deformation temperature ranges.

Figure 6:
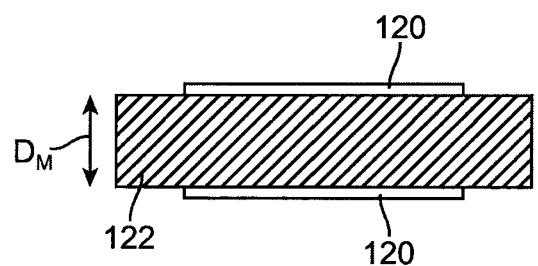
FIG. 6 depicts an axial cross-section of a polymer tube disposed over a mandrel with an inner diameter of the tube the same or substantially the same as an outer diameter of the mandrel.

A polymer construct may have a tendency to change shape when it is heated, such as during the annealing step. In particular a polymeric tube may tend to reduce in diameter or shrink upon heating. In some embodiments, the reduction in diameter of a polymer tube during the annealing step can be reduced or prevented. Reduction in diameter can be reduced or prevented by disposing a polymeric tube over a mandrel during the heating. The shrinkage of the tube is limited to the outside diameter of the mandrel. To prevent reduction in diameter, the inside diameter of the tube can be the same or substantially the same as the outside diameter of the mandrel. "Substantially the same" can refer to less than 0.1% difference. FIG. 6 illustrates this with an axial cross-section of a polymer tube 120 disposed over a mandrel 122. An inner diameter of tube 120 is the same or substantially the same as an outer diameter Dm of mandrel 122.

Figure 7A:
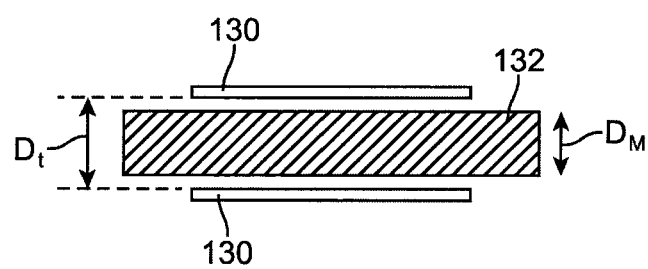
FIG. 7A depicts an axial cross-section of a polymer tube disposed over a mandrel with an inner diameter of the tube greater than an outer diameter of the mandrel.
Figure 7B:
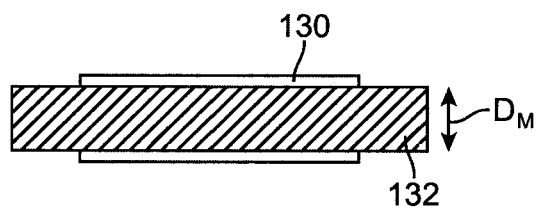
FIG. 7B shows the tube of FIG. 7A tube reduced in diameter due to heating.

To reduce shrinkage, the mandrel has an outside diameter less than the inside diameter of the polymer tube. FIG. 7A depicts this with an axial cross-section of a polymer tube 130 disposed over a mandrel 132. An inner diameter Dt of tube 130 is greater than an outer diameter Dm of mandrel 132. FIG. 7B shows that as tube 130 is heated during annealing, tube 130 can reduce in diameter, but that the reduction in diameter is limited to the outer diameter Dm of the mandrel.

In further embodiments, shrinkage can be reduced or prevented by maintaining an increased pressure within the tube during a post-deformation equilibration step until the tube is cooled below Tg. For example, the polymer tube can be disposed in a mold, e.g., glass, and the internal pressure is increased during heating by blowing a gas in the tube.

Figure 8A:
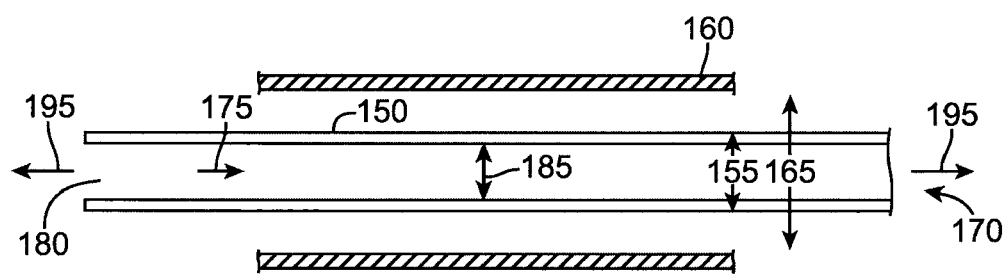
FIG. 8A depicts an axial cross-section of a polymeric tube positioned within a mold.
Figure 8B:
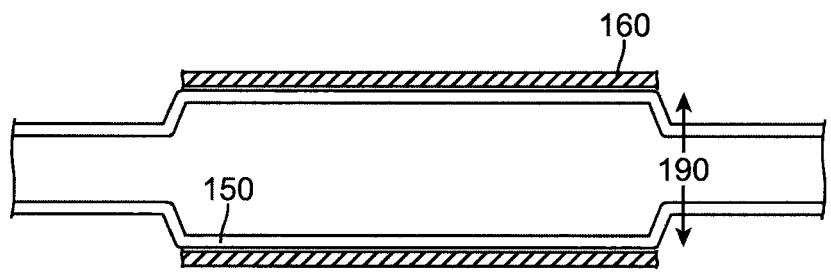
FIG. 8B depicts the polymeric tube of FIG. 8A in a radially deformed state.

As described above, a polymeric tube can be radially deformed using blow molding. FIGS. 8A-B illustrate an exemplary embodiment of deforming a polymeric tube using blow molding. FIG. 8A depicts an axial cross-section of a polymeric tube 150 with an outside diameter 155 positioned within a mold 160. Mold 160 limits the radial deformation of polymeric tube 150 to a diameter 165, the inside diameter of mold 160. Polymer tube 150 may be closed at a distal end 170 which may be open in subsequent manufacturing steps. A fluid is conveyed, as indicated by an arrow 175, into an open proximal end 180 of polymeric tube 150. A tensile force 195 can be applied at proximal end 180, a distal end 170, or both.

Polymeric tube 150 may be heated by heating the fluid to a temperature above ambient temperature prior to conveying the gas into polymeric tube 150. Alternatively, the polymeric tube may be heated by heating the exterior of mold 160 by blowing a warm gas on the mold. The tube may also be heated by a heating element in the mold or a lamp that directs heat on the mold such as an infra-red lamp providing infra-red energy.

The increase in pressure inside of polymer tube 150 facilitated by the increase in temperature of the polymeric tube causes radial deformation of polymer tube 150, as indicated by an arrow 185. FIG. 8B depicts polymeric tube 150 in a deformed state with an outside diameter 190 within mold 160.

In some embodiments, the tube may be expanded at the same time or about the same time along an entire axial length of the tube. In this case, the tube is heated uniformly or close to uniformly along the axial length. The tube then expands along this length when it reaches an expansion temperature close to or above Tg. Alternatively, the tube can expand sequentially along an axial length. In this case, a heating nozzle may translate along the axial length, heating the tube as it translates. The tube then expands as the nozzle translates and heats the tube.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Inside Diameter of Deformed Tube}}{\text{Original Inside Diameter of Tube}}$$

In some embodiments, the radial draw ratio of a polymeric tube for use in fabricating a stent may be between about 1 and 10, or more narrowly between about 2 and 6. Similarly, the degree of axial deformation may be quantified by an axial draw ratio:

$$\frac{\text{Length of Deformed Tube}}{\text{Original Length of Tube}}$$

In general, extrusion refers to the process of conveying a polymer melt through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the final tube product.

An extruder generally includes a barrel through which a polymer melt is conveyed from an entrance to an exit port. The polymer can be fed to the extruder barrel as a melt or in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is conveyed or pumped, for example, through the use of rotating screw(s). Representative examples of extruders for use with the present invention may include single screw extruders, intermeshing co-rotating and counter-rotating twin-screw extruders and other multiple screw elasticating extruders.

For the purposes of the present invention, the following terms and definitions apply:

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

Figure 9:
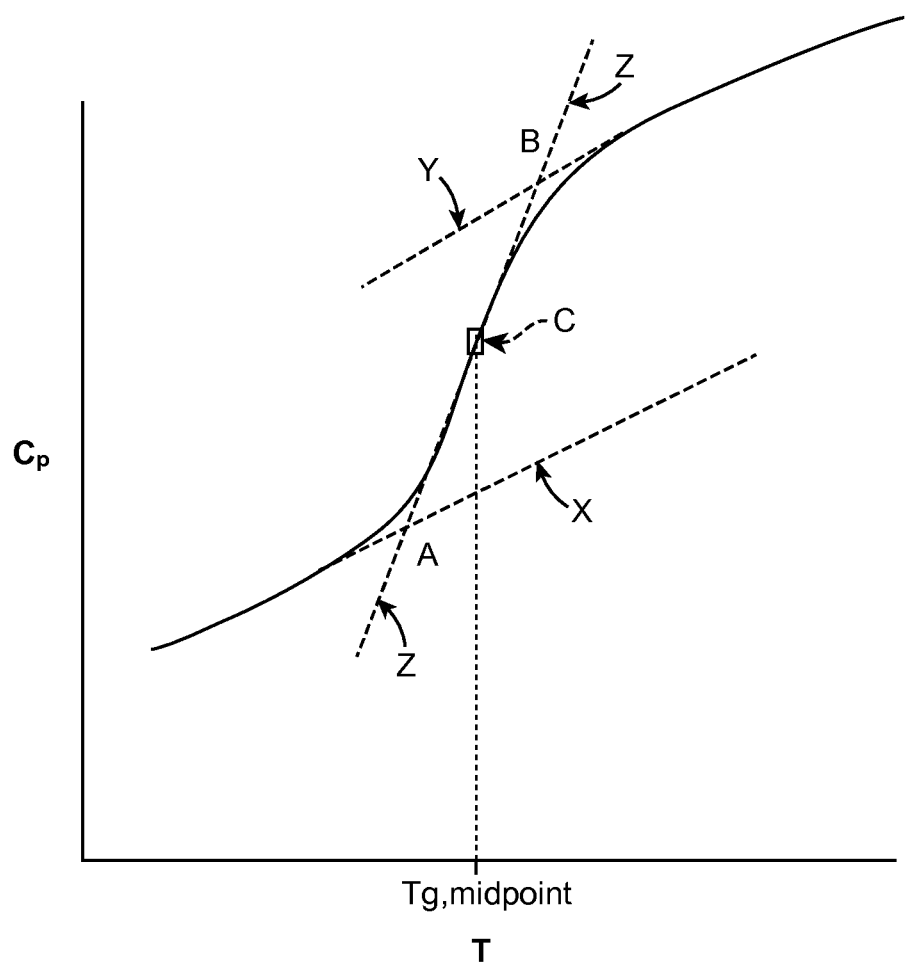
FIG. 9 illustrates the measurement of Tg from DSC which depicts the heat capacity vs. temperature in the region of the glass transition.

FIG. 9 illustrates the measurement of Tg from DSC which depicts the heat capacity vs. temperature in the region of the glass transition. As shown in FIG. 9, the heat capacity at low temperatures below the glass transition is linear and as the temperature increases there is a large increase in the slope with another linear region followed by a decrease in slope at higher temperature. The temperature range of change from where slope changes at low temperature, through the intermediate region to the change in slope at higher temperatures is the glass transition region. The glass transition temperature can be determined by extrapolating a line fit from the linear region at low temperature (line X), extrapolating a line fit from the linear region at high temperature (line Z), and a line fitted along the steep linear region (line Z) extrapolated to higher and lower temperatures so that. line Z intersects line X at A and line Y at B. The temperature at A is called Tg,onset and the temperature at B is Tg,end. The midpoint of Tg,onset and Tg along line Z (point C) is Tg,midpoint which is calculated from Tg,onset+½ (Tg,onset+Tg,end). Some sources defined the Tg as Tg,onset while other sources define Tg as Tg,midpoint. Unless otherwise specified, Tg refers to Tg,midpoint in the present application.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress-strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
   providing a polymer tube having a glass transition temperature (Tg);
   annealing the polymer tube at a temperature range of Tg−15° C. to Tg−5° C.,
   wherein the polymer tube is annealed for a selected annealing time greater than 1 min,
   wherein the annealing increases the nucleation density of the polymer tube;
   cooling the polymer tube to below 30° C. at the end of the selected annealing time;
   followed by heating and radially expanding the polymer tube,
   wherein the cooling of the polymer tube to below 30° C. is prior to the heating and the radially expanding,
   wherein the radial expansion induces crystallization in the polymer tube,
   wherein the increase in nucleation density due to the annealing results in the formation of a higher crystallite density and a decrease in the size of the crystallites as compared to a tube that has not been annealed; and
   fabricating a stent scaffolding from the expanded polymer tube.

2. The method of claim 1, wherein the selected annealing time is greater than 1 day.

3. The method of claim 1, wherein the selected annealing time is 1-30 days.

4. The method of claim 2, wherein the polymer tube prior to the annealing is less than 5% crystallinity.

5. The method of claim 2, wherein there is no increase in crystallinity of the polymer tube during the annealing.

6. The method of claim 2, wherein a diameter of the polymer tube is unchanged during the annealing.

7. The method of claim 2, wherein a temperature of the polymer tube during the radial expansion is greater than a Tg,midpoint of the polymer tube.

8. The method of claim 2, wherein the polymer comprises poly(L-lactide).

9. The method of claim 2, wherein the polymer comprises poly(L-lactide-co-caprolactone).

10. The method of claim 2, wherein the polymer comprises poly(L-lactide-co-glycolide).

11. The method of claim 2, wherein the polymer tube is formed by melt processing.

12. The method of claim 2, wherein the polymer tube is formed by extrusion.

13. The method of claim 2, wherein the polymer tube is formed by injection molding.

\* \* \* \* \*